United States Patent [19]

Matsushita et al.

[11] Patent Number: 4,847,424

[45] Date of Patent: Jul. 11, 1989

[54] METHOD OF PRODUCING ALDEHYDE COMPOUND

[75] Inventors: Hajime Matsushita, Yokohama; Makoto Shibagaki, Kawasaki; Kyoko Takahashi, Tokyo, all of Japan

[73] Assignee: Japan Tobacco Inc., Tokyo, Japan

[21] Appl. No.: 160,156

[22] Filed: Feb. 25, 1988

[30] Foreign Application Priority Data

Mar. 3, 1987 [JP] Japan .................... 62-46707

[51] Int. Cl.$^4$ ............................................. C07C 45/54
[52] U.S. Cl. ..................................... 568/484; 568/490
[58] Field of Search ................................ 568/484, 490

[56] References Cited

U.S. PATENT DOCUMENTS

| 3,867,459 | 2/1975 | Hoffmann et al. | 568/484 |
| 4,156,791 | 5/1979 | Childs | 568/484 |
| 4,760,196 | 7/1988 | Fukumoto et al. | 568/484 |

Primary Examiner—Werren B. Lone
Attorney, Agent, or Firm—Nixon & Vanderhye

[57] ABSTRACT

A carboxylic acid or its ester is reduced by formic acid in the presence of a hydrous metal oxide solid catalyst, to produce a corresponding aldehyde. Using this method, no harmful waste is by-produced, an aldehyde compound can be produced at relatively low cost, and the aldehyde produced can be easily recovered.

8 Claims, No Drawings

METHOD OF PRODUCING ALDEHYDE COMPOUND

BACKGROUND OF THE INVENTION

1. Field of the Invention

The present invention relates to a method of producing an aldehyde compound in which a carboxylic acid or its ester is reduced to prepare a corresponding aldehyde compound.

2. Description of the Related Art

Aldehyde compounds play an important role in the field of organic chemical industries. For example, they are widely used as the raw material for perfumes or as intermediates for medicines, agricultural chemicals, and the like. They are also used for producing a higher alcohol, through utilizing aldol condensation, or for producing alcohols by way of reduction. Since the aldehydo group is active, aldehyde compounds are also used for synthesizing fine chemicals.

Methods for industrially synthesizing an aldehyde compound includes the oxo process, which makes use of an olefin as a raw material, and causes carbon monoxide and hydrogen to react therewith, to synthesize an aldehyde. However, this method is normally used only for synthesizing a lower aldehyde, since it is difficult to synthesize a higher aldehyde or a branched aldehyde by using this method (see "INDUSTRIELLE ORGANISCHE CHEMIE" by K. Baiserumar, H. J. Alpe).

A method, generally called "partial oxidation", is often used to oxidize alcohol, thereby to synthesize an aldehyde compound on an industrial scale. This method uses, as an oxidizing agent, chromic acid, pyridinium chromate, pyridinium chlorochromate, manganese dioxide, or a combination of dimethyl sulfoxide and electrophilic reagent. However, when this method is used, the alcohol is all too readily oxidized to a carboxylic acid. It is difficult to stop the oxidation of the alcohol before the produced aldehyde is further oxidized to a carboxylic acid. In order to stop the oxidation at this time, reaction conditions, such as the temperature, the solvent, and the like, must be strictly controlled. Moreover, since this method entails the use of an oxidizing agent which contains a heavy metal such as chromium, manganese, or the like, this results, undesirably, in a large amount of harmful waste being produced as a by-product of the reaction.

Another method of industrially synthesizing an aldehyde compound has been reported, which reduces a carboxylic acid to an aldehyde ("Chemistry Letters", 1974, 1447). In this method, aminoalane prepared from a secondary amine such as N-methyl piperazine and an aluminum hydride is used as a reducing agent. However, the reducing agent is readily hydrolyzed by water and becomes inactive. In addition, the reducing agent is expensive, and must be used in an amount more than an equivalent amount, resulting in high producing cost. Furthermore, since the partial reduction method using aminoalane is a homogenous reaction as in the partial oxidation method of the alcohol, it is not easy to separate a produced aldehyde, and a countermeasure for preventing corrosion of a reaction apparatus is also necessary.

As other methods of reducing a carboxylic acid to synthesize an aldehyde, a method of performing reduction using Na-Hg (Ber. duet. chme. Ges. 41, 4147 (1908)), and a method of reducing a carboxylic acid by formic acid using manganese monoxide, titanium dioxide, or the like as a catalyst (Compt. rend. 154, 561 (1912), J.C.S.70, 86 (1943)), have been reported. However, the latter method has very low reduction activity except for salicylic acid.

Note that a method of reducing a carboxylic acid ester to produce an aldehyde is unknown.

SUMMARY OF THE INVENTION

It is, therefore, an object of the present invention to provide a method with which no harmful waste is by-produced, a produced aldehyde compound can be easily recovered, and an aldehyde compound can be produced at relatively low cost.

In order to achieve the above object, in the method of the present invention, a carboxylic acid or its ester (they will be referred to as a carboxylic compound hereinafter) is reduced by a reducing agent comprising formic acid in the presence of a solid catalyst comprising a hydrous metal oxide so as to produce a corresponding aldehyde compound.

DESCRIPTION OF THE PREFERRED EMBODIMENTS

A carboxylic acid or its ester (carboxylic compound) which is to be reduced to a corresponding aldehyde compound by the method of the present invention may include chain carboxylic acid, cyclic (alicyclic, aromatic, heterocyclic) carboxylic acid, or an ester thereof (except for formic acid). More specifically, preferable examples are: acetic acid and its ethyl ester; propionic acid, caproic acid, and their ethyl esters; capric acid and its ethyl ester; benzoic acid and its ethyl ester; cyclohexanecarboxylic acid and its ethyl ester; 2-methyl valeric acid and its ethyl ester; nicotinic acid, isonicotinic acid and their methyl esters; lauric acid, myristic acid, palmitic acid, stearic acid, and their ethyl esters; unsaturated aliphatic acids such as acrylic acid, oleic acid, and the like, and their ethyl esters.

In the method of the present invention, formic acid is used as a reducing agent serving as a hydrogen source. This is because formic acid is both inexpensive and is converted to harmless water and carbon dioxide after reducing a carboxylic compound.

In addition, a hydrous metal oxide, preferably hydrous zirconium oxide or hydrous tin oxide, is used as a catalyst. It should be noted that the term "hydrous metal oxide" means a material which has a metal-oxygen-metal bond and in which a hydroxyl group directly bonded to a metal remains, and does not mean a metal oxide having molecules of water such as water of crystallization, but can be rather considered as a partially dehydrated, condensation product made from a metal hydroxide. A hydrous metal oxide is a white-colored, hard amorphous solid, is insoluble in water or an organic solvent such as alcohol. This oxide is stable material and can be used as a heterogenous catalyst. A hydrous metal oxide can be prepared as follows:

A hydroxide is produced from an oxide, chloride, or salt of a metal, and is heat-treated to produce the hydrous matal oxide under conditions where the hydroxide is not completely dehydrated to an oxide. (If it is heat-treated at normal pressure and at a temperature of 500° C. or higher, the hydroxide will be completely dehydrated). When a heat treatment is performed at about 300° C., a stable, partially dehydrated hydroxide can be obtained. More specifically, when the hydroxide is heated at 300° C., a weight reduction of about 17% occurs in about one hour, and then no further weight reduction takes place. Zirconium or tin, both of which are relatively abundant minerals, are preferable as the raw material of the catalyst used in the method of this invention. When the hydrous metal oxide is used as the catalyst in the method of the invention, it may be ground into grains, and the grains may be used, with or without its grain size adjusted. The hydrous metal oxide may be supported on an appropriate carrier such as alumina, activated carbon, or the like.

In the method of the present invention, reduction of a carboxylic compound can be carried out in either a gaseous phase or a liquid phase.

When reduction is carried out in the gaseous phase, the hydrous metal oxide serving as the catalyst is placed in a reaction tube where it is kept at an appropriate reducing temperature. Then, a mixture composed of a carboxylic compound and formic acid as a reducing agent is supplied to the reaction tube, either directly or by using an inert carrier gas such as nitrogen, helium, or the like. The reaction mixture passing through a catalyst layer can be recovered as follows:

An outlet of the reaction tube is cooled by water, ice, or the like, to cause both the reaction product and any unreacted materials to condense. Water is subsequently removed from the recovered reaction mixture, by use of a known method, and the resultant mixture is distilled to obtain a desired aldehyde compound.

However, when this method is used, the carboxylic compound and the formic acid do not normally form a uniform solution. Therefore, both reactants should preferably be placed in a solvent—preferably tetrahydrofuran—which can dissolve them but which itself remains inactive during their reaction.

The reduction is preferably performed at a temperature of 250° C. to 400° C. and, more preferably, 300° C. to 380° C. 5 to 100 millimoles, and more preferably, 10 to 60 millimoles of formic acid are used per millimole of a carboxylic compound. A solvent for uniformly mixing the carboxylic compound and the formic acid is preferably added in the same amount as the formic acid. The reaction is preferably performed such that a solution mixture of reactants is supplied to the catalyst layer at a flow rate of 2 to 20 ml per hour and, more preferably, 5 to 10 ml per hour with respect to one gram of the catalyst.

When the reaction is performed in the liquid phase, the carboxylic compound and the formic acid are mixed at a mixing ratio as in the gaseous-phase reaction, and 1 to 3 g of a catalyst is added per 10 ml of the mixture of the reactants. Thereafter, the resultant mixture is reacted for 2 hours or more at a reaction temperature as in the gaseous-phase reaction. In this reaction, a solvent such as tetrahydrofuran inactive for the reaction can be added for the purpose of dilution. In order to achieve the reaction temperature, an autoclave or the like can be used as a reaction chamber.

In the reaction by the above methods, the carboxylic compound is not reduced to an alcohol.

The present invention will be described by way of its examples hereinafter.

EXAMPLE 1

In this example, 200 g of zirconium oxychloride octahydrate was dissolved in 10 ml of deionized water. A 1N sodium hydroxide aqueous solution was gradually added to the resultant solution under stirring, to adjust the pH of this solution to 6.8. The resultant hydrated gel was filtered to remove an excess solution of salts, and thereafter, the gel was repetitively washed with deionized water until no chlorine ions were detected in the washing solution.

The resultant gel was then cut into pieces which were left to dry at room temperature. When the dry gel pieces were immersed in deionized water, they abruptly broke up into granules having a wide range of grain sizes. These granules were filtered and once again left to dry at room temperature, which resulted in 90 g of granules being obtained. These granules were classified by sieving or the like, to recover those having grain sizes falling within a range of 24 to 60 mesh. These granules were heat-treated in a drying machine at a temperature of 300° C. for 5 hours, whereby a hydrous zirconium oxide catalyst was obtained.

EXAMPLE 2

In this example, 261 g of anhydrous tin tetrachloride was dissolved in 4 l of deionized water. A 28% ammonia water was gradually added to the solution, while stirring it well, thereby to adjust the pH of the solution to 7.0. The resultant gel was treated following the same procedures as in Example 1, whereby 141 g of granules were obtained. The granules were heat-treated in a drying machine at a temperature of 300° C. for 5 hours, and a hydrous tin oxide catalyst obtained.

EXAMPLE 3

In this example, 2.0 g of hydrous zirconium oxide obtained in Example 1 was placed in a heat-resistant glass tube (inner diameter, 4 mm; length, 50 cm), to form a layer about 15 mm deep, and were fixed. The glass tube was then placed in an electric furnace, and heated to 350° C. and was kept at this temperature.

Meanwhile, formic acid and n-caproic acid were mixed at a molar ratio of 30:1, and tetrahydrofuran equal in amount to the formic acid was added to the resultant mixture, to obtain a reaction mixture. In order to bring this solution into contact with the catalyst, the solution was injected, by means of a microfeeder, at a flow rate of 10 ml/hour in a nitrogen gas flow (0.5 ml/sec) at room temperature, and the resultant gas mixture was fed into the glass tube in the electric furnace. The material flowing out of the catalyst layer was condensed by means of water cooling at an outlet of the glass tube. The resultant solution was analyzed by gas chromatography, thereby determining the rate of conversion (i.e., the ratio (%) of the reaction product to the carboxylic acid used as raw material), and also the selectivity (i.e., the ratio (%) of the corresponding aldehyde to the reaction product). The results were as is shown in Table 1.

EXAMPLES 4–13

In these examples, the same procedures as used in Example 3 were followed, except that instead of n-caproic acid being used as the raw material carboxylic acid, cyclohexanecarboxylic acid, n-capric acid, 2-methyl-n-valeric acid, 2-ethylhexaic acid, 2-phenyl butyric acid, benzoic acid, adamantane-1-carboxylic acid, and pivalic acid were used (Examples 4–11), the reaction temperature was set at 300° C. instead of 350° C. (Example 12), and the molar ratio of the raw material carboxylic acid and the formic acid was set to 10:1 instead of 30:1 (Example 13). The results are summarized in Table 1.

EXAMPLES 14–17

In these examples also, the same procedures as used in Example 3 were followed, except that n-ethyl caproate, n-ethyl caprate, ethyl cyclohexanecarboxylate, and ethyl benzoate were used in place of n-caproic acid. The results are summarized in Table 1.

EXAMPLES 18–23

Under the same conditions as in Example 3—except that the hydrous tin oxide obtained in Example 2 was used as a catalyst—n-caproic acid, n-capric acid, cyclohexanecarboxylic acid, benzoic acid, ethyl cyclohexanecarboxylate, and ethylbenzoate were respectively

TABLE 1
GASEOUS-PHASE REDUCTION OF CARBOXYLIC ACIDS AND CARBOXYLIC ACID ESTERS USING HYDROUS ZIRCONIUM AS CATALYST

| Example No. | Raw Material Carboxylic Acid Ester | Produced Aldehyde | Molar Ratio | Temperature (°C.) | Rate of Conversion (%) | Selectivity (%) |
|---|---|---|---|---|---|---|
| 3 | n-pentyl–COOH | n-pentyl–CHO | 30:1 | 350 | 90 | 50 |
| 4 | cyclohexyl–COOH | cyclohexyl–CHO | 30:1 | 350 | 25 | 95 |
| 5 | n-nonyl–COOH | n-nonyl–CHO | 30:1 | 350 | 85 | 60 |
| 6 | (CH$_3$)$_2$CH–CH$_2$–CH(CH$_3$)–COOH (2-methyl branched) | corresponding –CHO | 30:1 | 350 | 40 | 90 |
| 7 | CH$_3$CH$_2$CH$_2$CH(C$_2$H$_5$)–COOH (2-ethyl branched) | corresponding –CHO | 30:1 | 350 | 25 | 73 |
| 8 | C$_6$H$_5$–CH(C$_2$H$_5$)–COOH | C$_6$H$_5$–CH(C$_2$H$_5$)–CHO | 30:1 | 350 | 25 | 73 |
| 9 | C$_6$H$_5$–COOH | C$_6$H$_5$–CHO | 30:1 | 350 | 40 | 88 |
| 10 | 1-adamantyl–COOH | 1-adamantyl–CHO | 30:1 | 350 | 6 | 75 |
| 11 | (CH$_3$)$_3$C–COOH | (CH$_3$)$_3$C–CHO | 30:1 | 350 | 5 | 60 |
| 12 | n-pentyl–COOH | n-pentyl–CHO | 30:1 | 300 | 54 | 72 |
| 13 | n-pentyl–COOH | n-pentyl–CHO | 10:1 | 350 | 60 | 50 |
| 14 | n-pentyl–COOC$_2$H$_5$ | n-pentyl–CHO | 30:1 | 350 | 91 | 44 |
| 15 | n-nonyl–COOC$_2$H$_5$ | n-nonyl–CHO | 30:1 | 350 | 90 | 60 |
| 16 | cyclohexyl–COOC$_2$H$_5$ | cyclohexyl–CHO | 30:1 | 350 | 88 | 33 |
| 17 | C$_6$H$_5$–COOC$_2$H$_5$ | C$_6$H$_5$–CHO | 30:1 | 350 | 70 | 18 | allowed to react with formic acid, and the rates of conversion and the selectivities were calculated. The results are summarized in Table 2.

hydrous zirconium oxide (Example 26). The results are summarized in Table 3.

TABLE 3

LIQUID-PHASE REDUCTION

| Example No. | Raw Material Carboxylic Acid/Ester | Produced Aldehyde | Reaction Condition Molar Ratio | Temperature (°C.) | Type of Metal of Catalyst | Rate of Conversion (%) | Selectivity (%) |
| --- | --- | --- | --- | --- | --- | --- | --- |
| 24 | ⌒⌒⌒COOH | ⌒⌒⌒CHO | 30:1 | 300 | Zr | 80 | 75 |
| 25 | ⬡—COOC$_2$H$_5$ | ⬡—CHO | 30:1 | 300 | Zr | 78 | 45 |
| 26 | ⌒⌒⌒COOH | ⌒⌒⌒CHO | 30:1 | 300 | Sn | 100 | 38 |

TABLE 2

GASEOUS-PHASE REDUCTION OF CARBOXYLIC ACIDS AND CARBOXYLIC ACID ESTERS USING HYDROUS TIN OXIDE AS CATALYST

| Example No. | Raw Material Carboxylic Acid Ester | Produced Aldehyde | Reaction Condition Molar Ratio | Temperature (°C.) | Rate of Conversion (%) | Selectivity (%) |
| --- | --- | --- | --- | --- | --- | --- |
| 18 | ⌒⌒COOH | ⌒⌒CHO | 30:1 | 350 | 98 | 70 |
| 19 | ⌒⌒⌒⌒COOH | ⌒⌒⌒⌒CHO | 30:1 | 350 | 99 | 65 |
| 20 | ⬡—COOH | ⬡—CHO | 30:1 | 350 | 94 | 70 |
| 21 | ⌾—COOH | ⌾—CHO | 30:1 | 350 | 84 | 55 |
| 22 | ⬡—COOC$_2$H$_5$ | ⬡—CHO | 30:1 | 350 | 80 | 40 |
| 23 | ⌾—COOC$_2$H$_5$ | ⌾—CHO | 30:1 | 350 | 91 | 41 |

EXAMPLE 24

In this example, 150 ml of formic acid and 5 ml of n-caproic acid were poured into a 100-ml stainless steel autoclave and then mixed. Then, 5 ml of tetrahydrofuran was added to the resultant mixture, to obtain a uniform solution. After 2.0 g of the hydrous zirconium oxide obtained in Example 1 was added as a catalyst to the solution, the resultant mixture was heated to 300° C. and allowed to react for 2 hours. Thereafter, the rate of conversion and the selectivity of the resultant solution were measured, the results being summarized in Table 3.

EXAMPLES 25 & 26

In these examples, the same procedures as used in Example 24 were followed, except that ethyl cyclohexanecarboxylate was used in place of n-caproic acid (Example 25) and hydrous tin oxide was used in place of hydrous zirconium oxide (Example 26). The results are summarized in Table 3.

According to the method of the present invention as described above, a corresponding aldehyde compound can be produced from a carboxylic compound at a relatively high yield.

In the method of the present invention, formic acid is used as a reducing agent. Not only is formic acid inexpensive, but it is converted to harmless water and carbon dioxide by the reaction. As a result, an aldehyde compound can be produced at relatively low cost, and without any harmful toxic substance as a by-product.

Since the method of the present invention makes use of hydrous metal oxide as a catalyst, and this hydrous metal oxide is a heterogeneous system, separation of the catalyst and recovery of the resultant aldehyde compound are both accomplished with ease.

What is claimed is:

1. A method of producing an aldehyde, which comprises reducing a carboxylic compound selected from the group consisting of an unsubstituted aliphatic or alicylic carboxylic acid having 2 to 18 carbon atoms, benzoic acid, 2-phenyl butyric acid, nicotinic acid, isonicotinic acid and esters thereof by a reducing agent comprising formic acid, in the presence of a solid catalyst comprising a hydrous metal oxide at a temperature falling within the range of 250° C. to 400° C. to produce a corresponding aldehyde.

2. A method according to claim 1, wherein the reduction is performed in a gaseous phase.

3. A method according to claim 1, wherein the reduction is performed in a liquid phase.

4. A method according to claim 1, wherein the solid catalyst is selected from the group consisting of hydrous zirconium oxide and hydrous tin oxide.

5. A method according to claim 1, wherein the carboxylic compound is selected from the group consisting of acetic acid and its ethyl ester; propionic acid, caproic acid, and their ethyl esters; capric acid and its ethyl ester; benzoic acid and its ethyl ester; cyclohexanecarboxylic acid and its ethyl ester; 2-methyl valeric acid and its ethyl ester; nicotinic acid, isonicotinic acid and their methyl esters; lauric acid, myristic acid, palmitic acid, stearic acid, and their ethyl esters, acrylic acid, oleic acid, and their thyl esters; 2-ethyl hexaic acid, 2-phenyl butyric acid and adamantane-1-carboxylic acid.

6. A method according to claim 1, wherein the carboxylic compound and the reducing agents are used at a molar ratio of 1:5 to 1:100.

7. A method according to claim 2, wherein a mixture is prepared in which a molar ratio of the carboxylic compound and the reducing agent is 1:5 to 1:100, and the mixture is brought into contact with 1 g of catalyst at a rate of 2 to 20 ml/hour.

8. A method according to claim 3, wherein a mixture is prepared in which a molar ratio of the carboxylic compound and the reducing agent is 1:5 to 1:100, and 1 to 3 g of a catalyst are used per 10 ml of the mixture.

* * * * *